US008775816B2

(12) United States Patent
Lopez et al.

(10) Patent No.: US 8,775,816 B2
(45) Date of Patent: Jul. 8, 2014

(54) METHOD AND APPARATUS TO ENHANCE SECURITY AND/OR SURVEILLANCE INFORMATION IN A COMMUNICATION NETWORK

(75) Inventors: José de Francisco Lopez, Aurora, IL (US); David S. Benco, Winfield, IL (US); Catriona M. Saunders, Framingham, MA (US)

(73) Assignee: Alcatel Lucent, Paris (FR)

( * ) Notice: Subject to any disclaimer, the term of this patent is extended or adjusted under 35 U.S.C. 154(b) by 157 days.

(21) Appl. No.: 13/007,878

(22) Filed: Jan. 17, 2011

(65) Prior Publication Data
US 2012/0183230 A1 Jul. 19, 2012

(51) Int. Cl.
*H04L 29/06* (2006.01)
*G06F 19/00* (2011.01)
*H04W 48/16* (2009.01)

(52) U.S. Cl.
CPC ........... *G06F 19/3493* (2013.01); *H04W 48/16* (2013.01)
USPC .......................................................... 713/178

(58) Field of Classification Search
CPC ........................... G06F 19/3493; H04W 48/16
USPC .......................................................... 713/178
See application file for complete search history.

(56) References Cited

U.S. PATENT DOCUMENTS

| 6,538,623 | B1 * | 3/2003 | Parnian et al. | 345/8 |
| 2008/0147826 | A1 * | 6/2008 | Velusamy et al. | 709/219 |
| 2010/0013931 | A1 * | 1/2010 | Golan et al. | 348/150 |

* cited by examiner

*Primary Examiner* — Hadi Armouche
*Assistant Examiner* — Dao Ho
(74) *Attorney, Agent, or Firm* — Fay Sharpe LLP

(57) ABSTRACT

Existing video surveillance security approaches enhanced with suitable functionality of the telecommunications wireless network are provided. Security personnel are equipped with hand-held devices capable of recording video, photos, audio, and text. This data is geo-tagged and time-stamped by the application and uploaded to the telecommunications network and stored in the network. As such, the geo-tagged, time-stamped information is immediately available to other investigators who are in the same geographic vicinity through access controls administered by a secure social network. The information may also be accessible from remote locations via the internet. All wireless and Internet communications may be protected using end-to-end secure transport layer communications protocols.

21 Claims, 4 Drawing Sheets

METHOD AND APPARATUS TO ENHANCE SECURITY AND/OR SURVEILLANCE INFORMATION IN A COMMUNICATION NETWORK

FIELD OF INVENTION

This invention relates to a method and apparatus to enhance information, such as security and/or surveillance information in a communication network.

While the invention is particularly directed to the art of gathering information for security, surveillance or evidentiary purposes, and will be thus described with specific reference thereto, it will be appreciated that the invention may have usefulness in other fields and applications.

BACKGROUND

By way of background, widespread installation of fixed-position video cameras in public places and inside of buildings has provided law enforcement and security personnel with valuable sources of information for gathering evidence. However, the information from these fixed-position cameras is limited to the field of view and perspective of the camera. As such, fixed-installation cameras are subject to vandalism. Also, these systems have a limited-term video archival period (typically 3-7 days) and supply only raw video—that is, un-annotated video. Thus, security personnel must manually review hours of video to gather evidence. In addition, the video footage from these cameras is not readily available to personnel at the site at times when the information may be most needed, such as during an initial or follow-up investigation. Repeated visits to the site, and/or repeated efforts to review the video or other physical media stored in vaults or file cabinets, are usually required.

As a result of these deficiencies of such known types of video surveillance systems, in traditional law enforcement practice, early observations by law enforcement personnel are not automatically linked to the investigation, nor are they available to other security personnel in the vicinity or the area of interest. Furthermore, the investigation materials (e.g., security personnel observations, photos, videos, annotations, witness statements, notes of investigative personnel, etc.) are not readily available to other field personnel in the same vicinity, even long after the event has occurred. Because of these limitations, correlations and insights that could prove to be very valuable are never discovered.

SUMMARY

A method and apparatus to enhance security and/or surveillance information are provided.

In one aspect of the invention, the method comprises recording real-time data regarding the area of interest or events occurring in the area of interest, providing a time-stamp for the recorded data, providing geolocation information for the recorded data, selectively annotating the recorded data with additional information, and, uploading the recorded data to a central network location.

In another aspect of the invention, the recorded data comprises at least one of video data, photographs, audio data and text data.

In another aspect of the invention, the recording is conducted by a mobile device.

In another aspect of the invention, the additional information comprises at least one of audio data, text data and audio-to-text converted data.

In another aspect of the invention, the uploading is conducted using a secure transport layer communication protocol.

In another aspect of the invention, the method further comprises performing digital analytics on the recorded data.

In another aspect of the invention the method comprises receiving recorded, selectively annotated real-time data regarding the area of interest or events occurring in the area of interest, the recorded data being provided with a time-stamp and geolocation information, and, maintaining the recorded, selectively annotated real-time data at a central network location accessible to a plurality of users.

In another aspect of the invention, the receiving is through a secure transport layer communication protocol.

In another aspect of the invention, the central network location is accessible by the plurality of users through a secure transport layer communication protocol.

In another aspect of the invention, the recorded, selectively annotated real-time data comprises at least one of video data, audio data, photographs, text and audio-to-text converted data.

In another aspect of the invention, the method further comprises selectively performing analytics on the recorded data.

In another aspect of the invention the device comprises a recording module operative to record real-time data regarding the area of interest or events occurring in the area interest, a time-stamped module operative to provide a time-stamp for the recorded data, a geolocation module operative to communication with a geolocation server to provide geolocation information to the recorded data, an annotation module operative to selectively incorporate additional information in the recorded data, and, an upload module operative to upload the recorded data.

In another aspect of the invention, the recorded data comprises at least one of video data, photographs, audio data and text data.

In another aspect of the invention, the device is implemented as a mobile device.

In another aspect of the invention, the system comprises a tagged digital media repository operative to receive recorded, selectively annotated real-time data regarding the area of interest or events occurring in the area of interest, the recorded data being provided with a time-stamp and a geolocation information, and maintaining the recorded selectively annotated real-time data, and, an analytics engine operative to selectively perform analytics on the recorded selectively annotated real-time data.

In another aspect of the invention, the system further comprises a geolocation server.

In another aspect of the invention, the system further comprises an encryption module.

In another aspect of the invention, the system further comprises a social network server.

In another aspect of the invention, the recorded, selectively annotated data comprises at least one of video data, photographs, audio data and text data.

In another aspect of the invention, the receiving is conducted using a secure transport layer communication protocol.

Further scope of the applicability of the present invention will become apparent from the detailed description provided below. It should be understood, however, that the detailed description and specific examples, while indicating preferred embodiments of the invention, are given by way of illustration only, since various changes and modifications within the spirit and scope of the invention will become apparent to those skilled in the art.

BRIEF DESCRIPTION OF THE FIGURES

Some embodiments of apparatus and/or methods in accordance with embodiments of the present invention are now described, by way of example only, and with reference to the accompanying drawings, in which.

DESCRIPTION OF EMBODIMENTS

According to the presently described embodiments, existing video surveillance and/or security approaches are enhanced with functionality and components of the telecommunications network. In this regard, in at least one form, security personnel are equipped with hand-held devices capable of recording video, photos, audio, and text (e.g., a smart phone) during normal security rounds or during crime scene investigation. In addition, all of this data is geo-tagged and time-stamped by the application and uploaded to the telecommunications network. As such, the geo-tagged, time-stamped information stored in the network is immediately available, e.g. wirelessly, to other investigators who are in the same geographic vicinity through access controls administered by, for example, a secure social network. The information is also accessible from remote locations (e.g., police headquarters) via the internet. In at least one form, all wireless and Internet communications are protected using end-to-end secure transport layer communications protocols, such as Secure Socket Layer (SSL).

Figure 1:
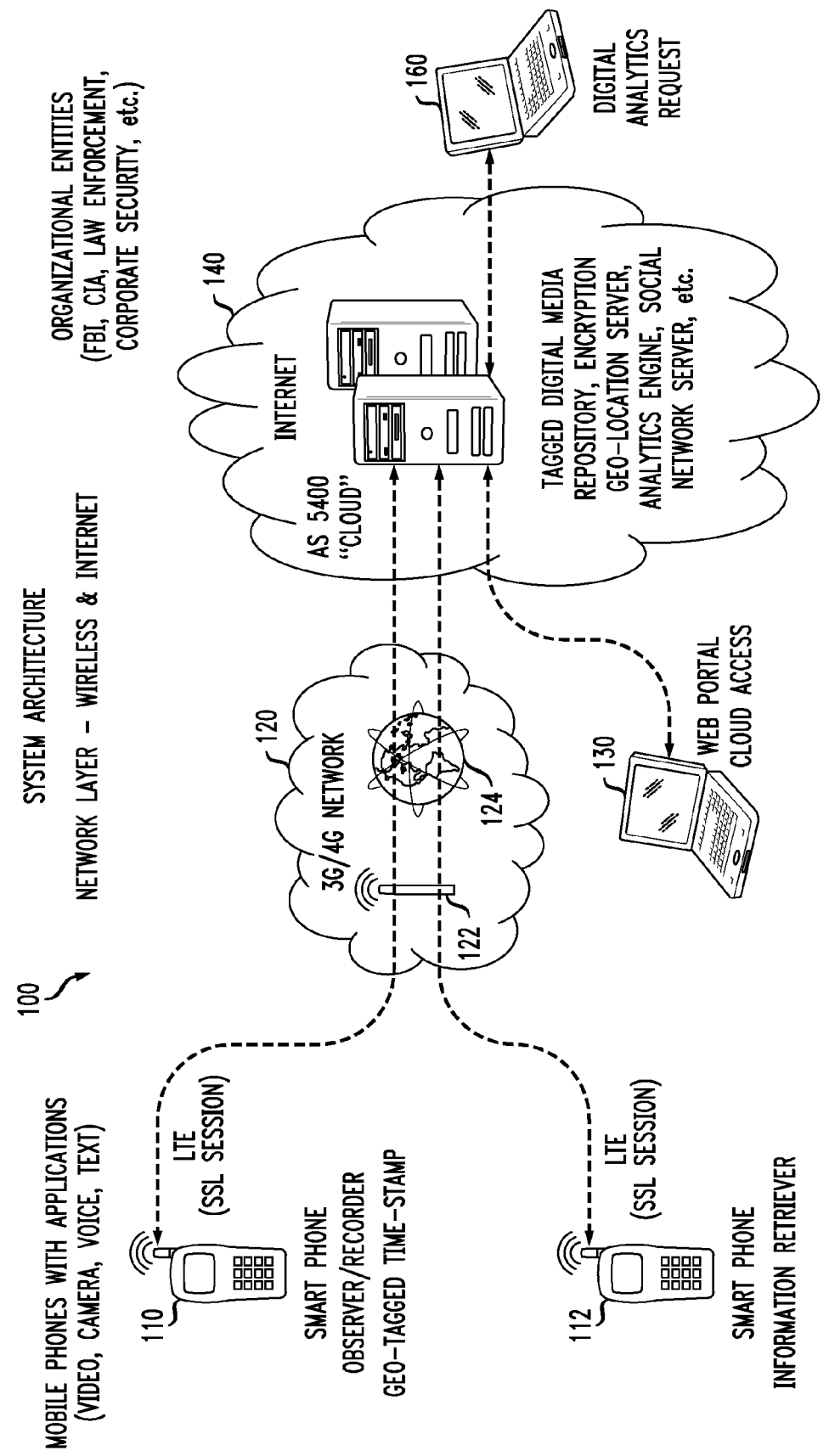
FIG. 1 illustrates a system into which the presently described embodiments may be implemented.

Referring now to the drawings wherein the showings are for purposes of illustrating the exemplary embodiments only and not for purposes of limiting the claimed subject matter, FIG. 1 provides a view of a system into which the presently described embodiments may be incorporated. As shown, a system 100 includes a plurality of mobile devices such as exemplary mobile devices 110 and 112. It should be appreciated these mobile devices may take a variety of forms and may perform a variety of functions. For example, the mobile devices may be smart phones that perform selective functionality as will be described, for example, in connection with FIG. 2. In at least one form, however, the mobile devices 110 or 112 may function as an observer or recorder of information, wherein recorded information is geo-tagged and/or time-stamped. In other situations, the mobile devices 110 or 112 may serve as an information retriever to assist with, for example, digital analytics that are being performed on recorded data stored in the network in accord with the presently described embodiments. For example, the user station 160 may issue a digital analytics request in connection with the presently described embodiments.

Also shown in FIG. 1 is an example network, e.g. 3G/4G network, that includes a base station device 122 and switching elements 124, both of which are merely representatively shown. A web portal access node 130 is shown and, in at least one form, provides a user with access to a network architecture 140. The network architecture 140 may take a variety of forms, as will be described in greater detail in connection with FIG. 4. Also, a user station 160 is shown. The user station 160 may be implemented by a variety of users that have access to the system functionality and the information generated according to the presently described embodiments.

It should be appreciated that the system 100 illustrated in FIG. 1 is merely exemplary in nature. Also, all elements of a surveillance and/or security system, as well as a communications network, are not shown for ease of reference.

Figure 2:
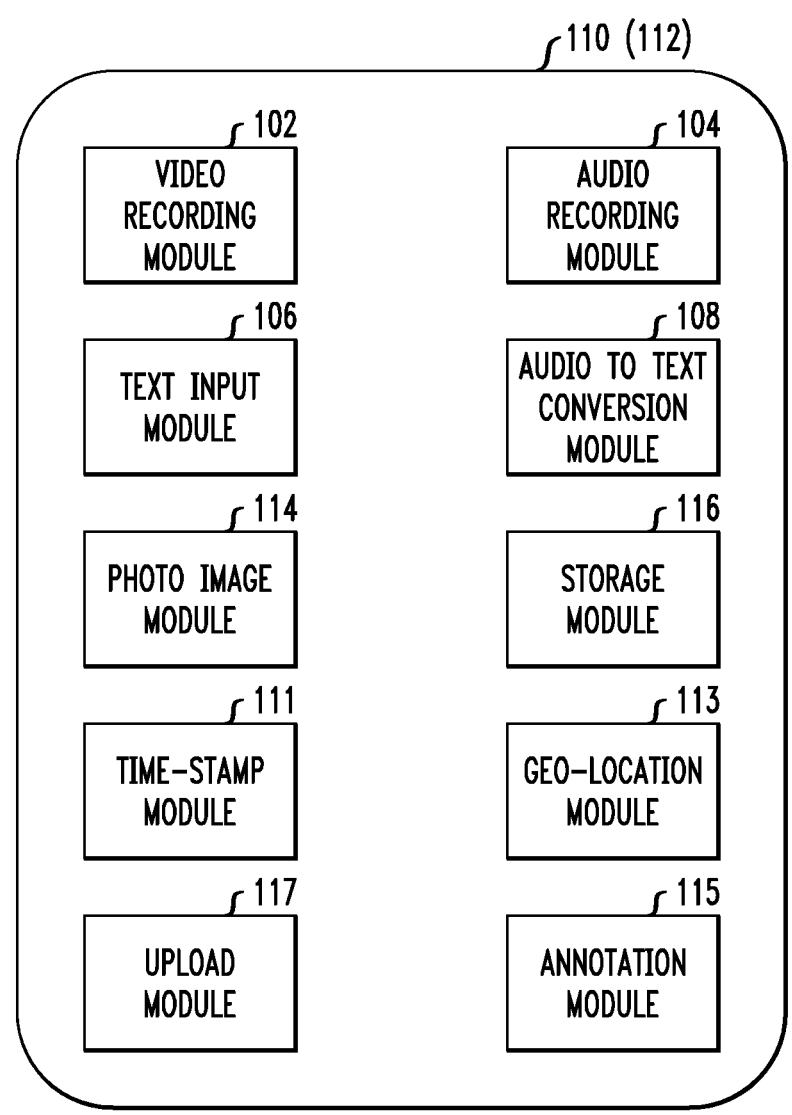
FIG. 2 illustrates an example device according to the presently described embodiments.

With reference now to FIG. 2, an example configuration for a mobile device according to the presently described embodiments (e.g. mobile devices 110 or 112) is shown. It should be appreciated that all circuitry and/or configurations (such as certain conventional circuitry and/or configurations) of the mobile device are not included in the drawing for ease of reference. However, according to the presently described embodiments, a suitable mobile device will be provided with, at least in one form, a video recording module 102, an audio recording module 104, a text input-module 106, an audio-to-text conversion module 108 and a photo image module 114. These modules are provided to allow users in an area of interest to gather data. Such areas of interest may include security zones or crime scenes. Also shown in FIG. 2 is a storage module 116. The storage module 116 is operative to store the data recorded by the aforementioned modules.

Figure 4:
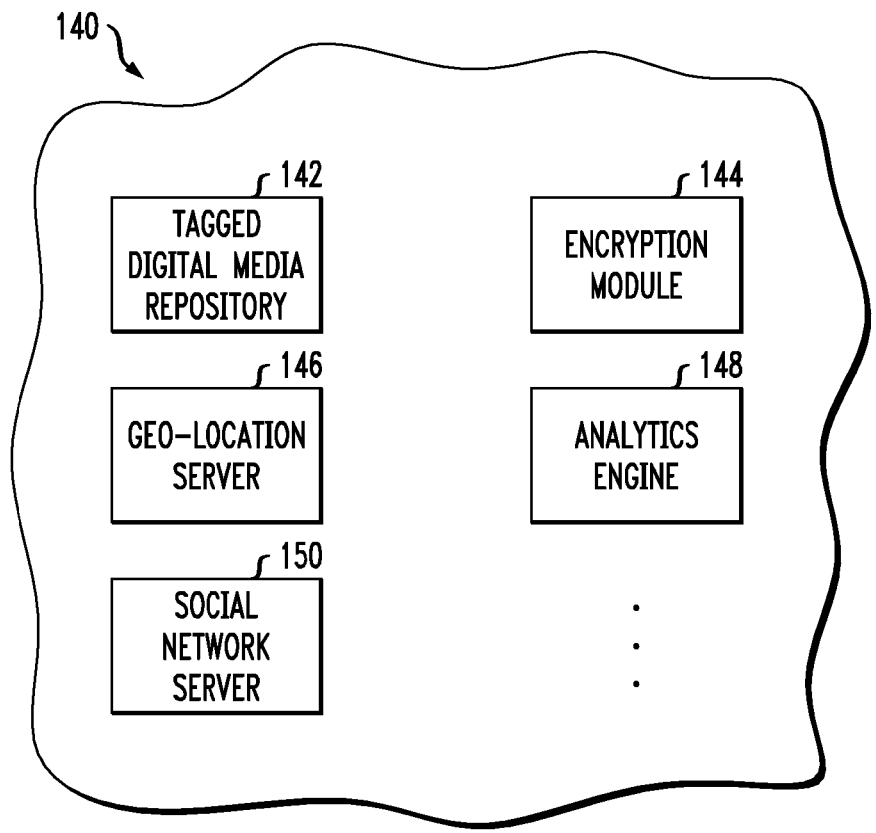
FIG. 4 illustrates an example network structure according to the presently described embodiments; and, FIG. 5 is a flow chart for an exemplary method according to the presently described embodiments.

Also shown in FIG. 2 are a time-stamp module 111 and a geolocation module 113. It should be appreciated that the data recorded by the modules 102, 104, 106, 108 and 114, are time-stamped and provided with geolocation information according to the presently described embodiments. The time-stamp module 111 may use information in the mobile device to develop the data for the time-stamp, or may retrieve information from a third party source. In at least in one form, the geolocation module 113 accesses a geolocation server (e.g. as shown in FIG. 4) in a remote location to provide geolocation information for the recorded data. Of course, it will be appreciated that the precise configuration and functionality will vary as a function of the sophistication of the mobile device and the supporting network. For example, a mobile device taking the form of a smartphone resembling the configuration of FIG. 2 will be able to provide both the geo-tagging and time-stamp information according to the presently described embodiments. Older, more traditional mobile devices (e.g., devices lacking GPS capability) may require different and/or additional network resources to accomplish the noted functionality according to the presently described embodiments.

Also shown is an annotation module 115. Annotation module 115 is operative to use, for example, audio recording module 104, text input module 106 or audio-to-text conversion module 108 to annotate the recorded data with additional information that may be helpful to security personnel and/or investigators in connection with the area of interest. The annotation module 115 allows for additional information to be recorded or input by the user to augment or supplement the information recorded in real-time. It should be appreciated that the annotation of additional information may be provided during a real-time recording of data or subsequent to recording of real-time data. It should be appreciated that the annotations, for all practical purposes, are incorporated as part of the recorded data for ease of processing and/or analytics. The annotations, in alternative forms, may also be maintained as separate files that are correlated to the recorded data file.

Also shown in FIG. 2 is an upload module 117. The upload module 117 is operative to upload the recorded real-time data, as well as any additional information that is incorporated or annotated therein, to the network for subsequent processing and/or use.

Figure 3:
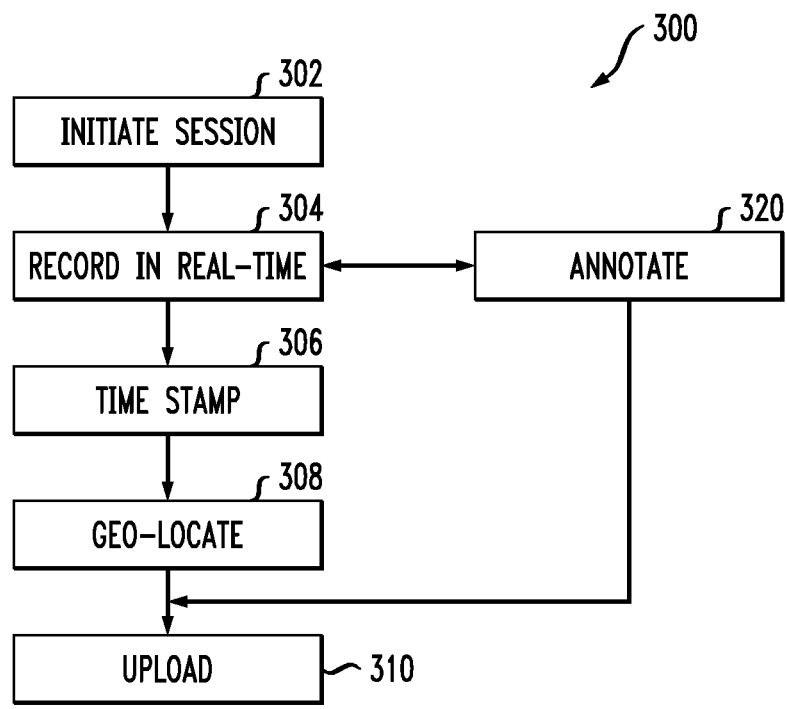
FIG. 3 is a flow chart for an exemplary method according to the presently described embodiments.

With reference now to FIG. 3, an example method 300, performed by a device such as mobile device 110 or 112 according to the presently described embodiments, begins with a session initiated by a user to gather and annotate information (at 302). The user then begins recording data in real-time (at 304). As noted above, it will be appreciated that the recording of data may include recording video data, recording audio data, inputting text information, providing audio data to be converted to text information or obtaining photo image data. This recording may occur during, for example, security rounds, or a crime scene investigation, in an area of interest. The recording may also relate to events occurring in an area of interest.

The recorded data is then time-stamped (at 306). Next, geolocation information is also provided to the data (at 308). As described above, the recorded information may then be uploaded to the network (at 310).

It should be understood that the data recorded in real-time may also be selectively annotated by the user (at 320). The annotations are incorporated into the recorded data and uploaded therewith (at 310). Again, it should be appreciated that the annotations may be provided to the recorded data at various times in the process. So, in some forms, the annotations may also be time-stamped and provided with geolocation information. It should also be appreciated that annotations are not necessary for an upload of recorded data to be accomplished.

With reference to FIG. 4, the network architecture 140 is illustrated. The network architecture could be implemented in a variety of manners. For example, the components described hereafter could be implemented on a single server or platform, or distributed on multiple servers or platforms. In at least one form, the network architecture 140 includes a tagged digital media repository 142. The digital media repository is operative to receive recorded, selectively annotated real-time data, as described above, regarding the area of interest or events occurring in the area of interest. In at least one form, as above, the recorded data is provided with a time-stamp and geolocation information. The tagged digital media repository also maintains the recorded, selectively annotated real-time data at a central location and is accessible to a plurality of users.

Also shown are an encryption module 144, a geolocation server 146, an analytics engine 148 and a social network server 150.

The encryption module 144 is operative to enhance security of the network architecture given the sensitive nature of the stored information. The geolocation server 146 is operative to provide information to the mobile devices, as described above, to enhance the recorded real-time data with geolocation information. The social network 150 is provided to allow user access to the digital media repository. It will be appreciated that the social network server 150 may take a variety of forms and include a variety of security functions.

It will be appreciated that the present system allows for, in at least one form, all communications to be accomplished in a secure manner by using a secure transport layer communication protocol such as a secure socket layer (SSL). The security, is of course, applicable to the social network server or any other server that is used to access the information in the tagged digital media repository. This security may also apply to all uploading of information.

Also, the analytics engine 148 is operative to receive digital analytics requests from any of a variety of sources including the user terminal 160 (FIG. 1). The analytics engine performs a variety of different functions (e.g., data mining and/or correlation analysis) on the tagged digital media repository to assist in security processes.

Figure 5:
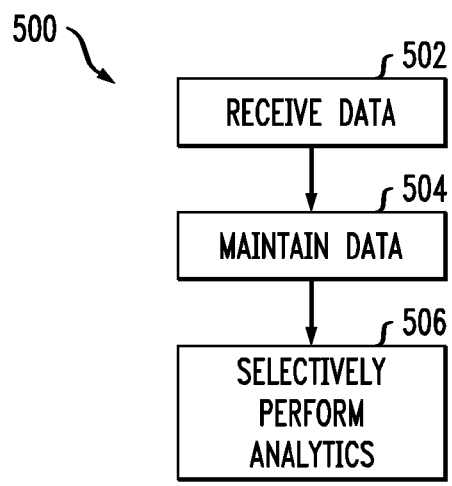

In operation, the network architecture 140 may function in a variety of manners. In one form, as shown in FIG. 5, a method 500 may be implemented by the system (e.g., be the tagged digital media repository and/or the analytics engine, or by other suitable control processors or modules in the system). In this regard, the tagged digital media repository, or other input module, receives recorded and selectively annotated data from mobile users (at 502). This data is maintained (at 504) in the digital media repository 142 for subsequent use and processing. In one form, the analytics engine 148 performs analytics on the stored data (at 506).

The invention offers advantages of co-locating all of the information—before an event (digital bread crumbs), during the investigation of an event (digital fingerprints), and subsequent review/analysis of an event (digital analytics).

Before the Event:

Security/law enforcement personnel may record observations in an area of interest (or about events occurring in such an area of interest) via video, photo, audio, or possibly annotated with, for example, voice to text data. These "digital bread crumbs" are geo-tagged and time-stamped and uploaded to network-based storage (e.g. the tagged digital media repository).

During the Event:

During investigation at a crime scene or area of interest, the evidence is gathered in video/photo/voice/text (e.g., witness statements, visual images, officer notes, etc.) and uploaded to the appropriate network elements, such as repository 142. During the investigation, previously geo-tagged information from this location is readily available.

After the Event:

Co-location of all relevant information from the location (e.g. via geo-tagging) and any suitable timeframe (e.g. via time-stamp) is available for subsequent analysis ("digital analytics").

This more complete and enhanced set of digital media available, according to the presently described embodiments, provides a much richer database for analysis, thus facilitating early crime detection and prevention via cloud computing analytics of multiple events.

The presently described embodiments provide a way to improve the effectiveness of criminal/security investigations by automatically linking all geographically and time-relevant information together, and making that information available to local field personnel and central office personnel in real-time. In addition, because the information database is much richer, improved results from analytics enable more effective crime prevention.

The presently described embodiments provide the ability to correlate all relevant information from an event based on geo-location, time, etc. All event information is available to field personnel and central locations in a secure fashion via social network architecture. Digital bread crumbs can be annotated and correlated with other officers' observations in real-time. Transition of crime scene investigation knowledge from disparate physical media stored in file cabinets to correlated digital fingerprints stored in the network cloud, suitable for more powerful analytics, is provided, resulting in more useful output. Increased efficiency from transcription of handwritten notes to automatic voice-to-text conversion of interviews is realized. The present application also results in reducing the amount of paper, travel, and other carbon-emissions-related activities in law enforcement and security applications.

A person of skill in the art would readily recognize that steps of various above-described methods can be performed by programmed computers or similar devices. In this regard, a variety of hardware configurations and/or software routines may be implemented. Herein, some embodiments are also intended to cover program storage devices, e.g. digital data storage media, which are machine or computer readable and encode machine-executable or computer-executable programs of instructions, wherein said instructions perform some or all of the steps of said above-described methods. The program storage devices may be, e.g. digital memories, magnetic storage media such as magnetic disks and magnetic tapes, hard drives, or optically readable digital data storage media. The embodiments are also intended to cover computers programmed to perform said steps of the above-described methods.

The functions of the various elements shown in the Figures, including any functional blocks labeled as modules, may be provided through the use of dedicated hardware, as well as hardware capable of executing software in association with appropriate software. When provided by a processor, the functions may be provided by a single dedicated processor, by a single shared processor, or by a plurality of individual processors, some of which may be shared. Moreover, explicit use of the term "module," "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non-volatile storage. Other hardware, conventional and/or custom, may also be included. Similarly, any switches shown in the Figures, are conceptual only. Their function may be carried out through the operation of program logic, through dedicated logic, through the interaction of program control and dedicated logic, or even manually, the particular technique being selectable by the implementer as more specifically understood from the context.

The above description merely provides a disclosure of particular embodiments of the invention and is not intended for the purposes of limiting the same thereto. As such, the invention is not limited to only the above-described embodiments. Rather, it is recognized that one skilled in the art could conceive alternative embodiments that fall within the scope of the invention.

We claim:

1. A method for enhancing security in an area of interest, the method comprising:
    recording real-time data to form one or more recorded file at a mobile device, wherein the recorded data relates to at least one of an area of interest, an event occurring in the area of interest, a subsequent investigation of the area of interest, and a subsequent investigation of the event;
    providing at least one time-stamp for the recorded data in the one or more recorded file;
    obtaining geolocation information associated with the recording of the real-time data and providing geo-tag information for the recorded data in the one or more recorded file;
    selectively annotating the recorded data with additional information to augment or supplement the recorded data with at least one of observations, statements, and notes by one or more person associated with at least one of the area of interest, the event, and the subsequent investigation; and,
    uploading the one or more recorded file and the corresponding annotations from the mobile device to a network-based storage device;
    wherein at least a portion of the corresponding annotations of the recorded data are incorporated in the one or more recorded file uploaded to the network-based storage device.

2. The method as set forth in claim 1 wherein the additional information comprises at least one of audio data, text data and audio-to-text converted data.

3. The method as set forth in claim 1 wherein at least a portion of the corresponding annotations of the recorded data are based on selective annotation of the recorded data during the recording of the real-time data.

4. The method as set forth in claim 1 wherein at least a portion of the corresponding annotations of the recorded data are provided subsequent to the recording of the real-time data.

5. The method as set forth in claim 1 wherein at least a portion of the corresponding annotations of the recorded data are maintained in one or more annotation file separate from the corresponding recorded file.

6. The method as set forth in claim 5, further comprising:
    providing at least one time-stamp for the additional information in the one or more annotation file; and
    obtaining geolocation information associated with the annotating of the recorded data and providing geo-tag information for the additional information in the one or more annotation file.

7. A method for enhancing security in an area of interest, the method comprising:
    receiving one or more recorded file and corresponding annotations from a mobile device at a network-based storage device, wherein the one or more recorded file includes recorded data with time-stamp and geo-tag information, wherein the recorded data relates to at least one of an area of interest, an event occurring in the area of interest, a subsequent investigation of the area of interest, and a subsequent investigation of the event, wherein the corresponding annotations are based on selective annotation of the recorded data with additional information to augment or supplement the recorded data with at least one of observations, statements, and notes by one or more person associated with at least one of the area of interest, the event, and the subsequent investigation; and,
    maintaining the one or more recorded file and the corresponding annotations at the network-based storage device;
    wherein the network-based storage device is configured such that the one or more recorded file and corresponding annotations are accessible to an authorized user associated with at least one of the area of interest, the event, and the subsequent investigation;
    wherein at least a portion of the corresponding annotations of the recorded data are incorporated in the one or more recorded file received from the mobile device.

8. The method as set forth in claim 7 wherein the network-based storage device is accessible to the authorized user through a secure transport layer communication protocol.

9. The method as set forth in claim 7 further comprising selectively performing analytics on the recorded data and the additional information.

10. The method as set forth in claim 7 wherein at least a portion of the corresponding annotations of the recorded data are maintained in one or more annotation files separate from the corresponding recorded file.

11. The method as set forth in claim 7 wherein at least a portion of the corresponding annotations of the recorded data are based on selective annotation of the recorded data during its initial recording by the mobile device.

12. The method as set forth in claim 7 wherein at least a portion of the corresponding annotations of the recorded data are maintained in one or more annotation file separate from the corresponding recorded file, the method further comprising:

receiving the one or more annotation file from the mobile device at the network-based storage device, wherein the one or more annotation file includes said portion of the corresponding annotations with time-stamp and geo-tag information.

13. A mobile device for enhancing security in an area of interest, the mobile device comprising:

a data recorder configured to record real-time data to form one or more recorded file, wherein the recorded data relates to at least one of an area of interest, an event occurring in the area interest, a subsequent investigation of the area of interest, and a subsequent investigation of the event;

a time-stamp processor configured to provide at least one time-stamp for the recorded data in each the one or more recorded file;

a geolocation receiver configured to obtain geolocation information associated with the recording of the real-time data and to provide geo-tag information for the recorded data in the one or more recorded file;

an annotation processor configured to selectively annotate the recorded data with additional information to augment or supplement the recorded data with at least one of observations, statements, and notes by one or more person associated with at least one of the area of interest, the event, and the subsequent investigation; and, an upload communication interface configured to upload the one or more recorded file and the corresponding annotations to a network-based storage device;

wherein the annotation processor and upload communication interface are configured such that at least a portion of the corresponding annotations of the recorded data are incorporated in the one or more recorded file uploaded to the network-based storage device.

14. The mobile device as set forth in claim 13 wherein the data recorder is configured such that the recorded data comprises at least one of video data, photographs, audio data and text data.

15. The mobile device as set forth in claim 13 wherein the data recorder and the annotation processor are configured such that at least a portion of the corresponding annotations of the recorded data are based on selective annotation of the recorded data during the recording of the real-time data.

16. The mobile device as set forth in claim 13 wherein the data recorder and annotation processor are configured such that at least a portion of the corresponding annotations of the recorded data are maintained in one or more annotation file separate from the corresponding recorded file.

17. The mobile device as set forth in claim 16 wherein the time-stamp processor is configured to provide at least one time-stamp for the additional information in the one or more annotation file;

wherein the geolocation receiver is configured to obtain geolocation information associated with the annotating of the recorded data and to provide geo-tag information for the additional information in the one or more annotation file;

wherein the upload communication interface is configured to upload the one or more annotation file to the network-based storage device.

18. A system for enhancing security in an area of interest, the system comprising:

a media repository configured to receive one or more recorded file and corresponding annotations from a mobile device, wherein the one or more recorded file includes recorded data with time-stamp and geo-tag information, wherein the recorded data relates to at least one of an area of interest, an event occurring in the area of interest, a subsequent investigation of the area of interest, and a subsequent investigation of the event, wherein the corresponding annotations are based on selective annotation of the recorded data with additional information to augment or supplement the recorded data with at least one of observations, statements, and notes by one or more person associated with at least one of the area of interest, the event, and the subsequent investigation, wherein the media repository is also configured to maintain the one or more recorded file and corresponding annotations; and, an analytics engine configured to selectively perform analytics on the recorded data and the additional information;

wherein the media repository is configured such that the one or more recorded file and corresponding annotations are accessible to an authorized user associated with at least one of the area of interest, the event, and the subsequent investigation;

wherein at least a portion of the corresponding annotations of the recorded data are incorporated in the one or more recorded file received from the mobile device.

19. The system as set forth in claim 18 further comprising a geolocation server configured to provide the mobile device with access to geolocation information for use by the mobile device in conjunction with providing the geo-tag information for the recorded data in the one or more recorded file.

20. The system as set forth in claim 18 wherein at least a portion of the corresponding annotations of the recorded data are based on selective annotation of the recorded data during its initial recording by the mobile device.

21. The system as set forth in claim 18 wherein at least a portion of the corresponding annotations of the recorded data are maintained by the mobile device in one or more annotation file separate from the corresponding recorded file;

wherein the media repository is configured to receive the one or more annotation file from the mobile device, wherein the one or more annotation file includes said portion of the corresponding annotations with time-stamp and geo-tag information.

* * * * *